(12) United States Patent
Hsu et al.

(10) Patent No.: US 11,123,266 B2
(45) Date of Patent: Sep. 21, 2021

(54) CONCEALABLE FEEDING TUBE ASSEMBLY

(71) Applicant: Jui-Che Hsu, Kaohsiung (TW)

(72) Inventors: Jui-Che Hsu, Kaohsiung (TW); Ping-Yi Hsu, Kaohsiung (TW); Chang-Bih Shie, Tainan (TW); Jui-Ting Hsu, Kaohsiung (TW)

(73) Assignee: Jui-Che Hsu, Kaohsiung (TW)

( * ) Notice: Subject to any disclaimer, the term of this patent is extended or adjusted under 35 U.S.C. 154(b) by 94 days.

(21) Appl. No.: 16/408,845

(22) Filed: May 10, 2019

(65) Prior Publication Data
US 2019/0343729 A1 Nov. 14, 2019

(30) Foreign Application Priority Data
May 10, 2018 (TW) .................. 107115992

(51) Int. Cl.
*A61J 15/00* (2006.01)
*A61M 39/20* (2006.01)

(52) U.S. Cl.
CPC .......... *A61J 15/0003* (2013.01); *A61M 39/20* (2013.01); *A61J 2205/20* (2013.01)

(58) Field of Classification Search
CPC ................ A61J 2205/20; A61J 15/0003; A61J 15/0053; A61J 15/0057; A61J 15/0034; A61M 2025/0226; A61M 2025/0233; A61M 2025/024; A61M 2210/0618; A61M 39/20
See application file for complete search history.

(56) References Cited

U.S. PATENT DOCUMENTS

| 3,568,678 | A | * | 3/1971 | Pourquier | ............. | A61M 31/00 |
| | | | | | | 604/174 |
| 4,175,564 | A | * | 11/1979 | Kwak | ............... | A61M 25/0668 |
| | | | | | | 604/171 |
| 4,547,192 | A | * | 10/1985 | Brodsky | ............. | A61J 15/0003 |
| | | | | | | 604/270 |
| 4,660,555 | A | * | 4/1987 | Payton | ............. | A61M 16/0488 |
| | | | | | | 128/207.18 |
| 5,792,119 | A | | 8/1998 | Marx | | |
| 9,504,630 | B2 | | 11/2016 | Liu | | |
| 2006/0129092 | A1 | * | 6/2006 | Hanlon | ............... | A61J 15/0092 |
| | | | | | | 604/93.01 |
| 2013/0338521 | A1 | * | 12/2013 | Thompson | ........ | A61M 16/0484 |
| | | | | | | 600/532 |

FOREIGN PATENT DOCUMENTS

| JP | H08-506249 | A | 7/1996 |
| TW | 201038264 | A | 11/2010 |
| TW | M558628 | U | 4/2018 |
| WO | WO2008112662 | A2 | 9/2008 |

* cited by examiner

*Primary Examiner* — Nathan R Price
*Assistant Examiner* — Courtney B Fredrickson
(74) *Attorney, Agent, or Firm* — Alan D. Kamrath; Karin L. Williams; Mayer & Williams PC (57) ABSTRACT

A concealable feeding tube assembly includes a tube and a removable member. The tube has an insertion portion and a feeding portion respectively at two ends thereof. The feeding portion is configured for insertion into a nasal cavity of a patient and intercommunicates with the insertion portion. The removable member is detachably attached to the tube and is configured to seal the feeding portion. The removable member includes an abutment portion extending beyond a lateral face of the removable member.

9 Claims, 10 Drawing Sheets

CONCEALABLE FEEDING TUBE ASSEMBLY

CROSS REFERENCE TO RELATED APPLICATION

The application claims the benefit of Taiwan application serial No. 107115992, filed on May 10, 2018, and the entire contents of which are incorporated herein by reference.

BACKGROUND OF THE INVENTION

1. Field of the Invention

The present invention generally relates to a feeding tube assembly and, more particularly, to a concealable feeding tube assembly that assists the patient in obtaining the nutrition without affecting his/her appearance.

2. Description of the Related Art

Feeding tubes have been clinically used for patients who are unable to take a meal as a result of faintness or stroke, or cannot absorb sufficient nutrition due to insufficient diet or esophagus disease. The feeding tube can assist the patient in obtaining the required nutrition by supplying the nutrition to the stomach of the patient at a fixed time and fixed amount.

Figure 1:
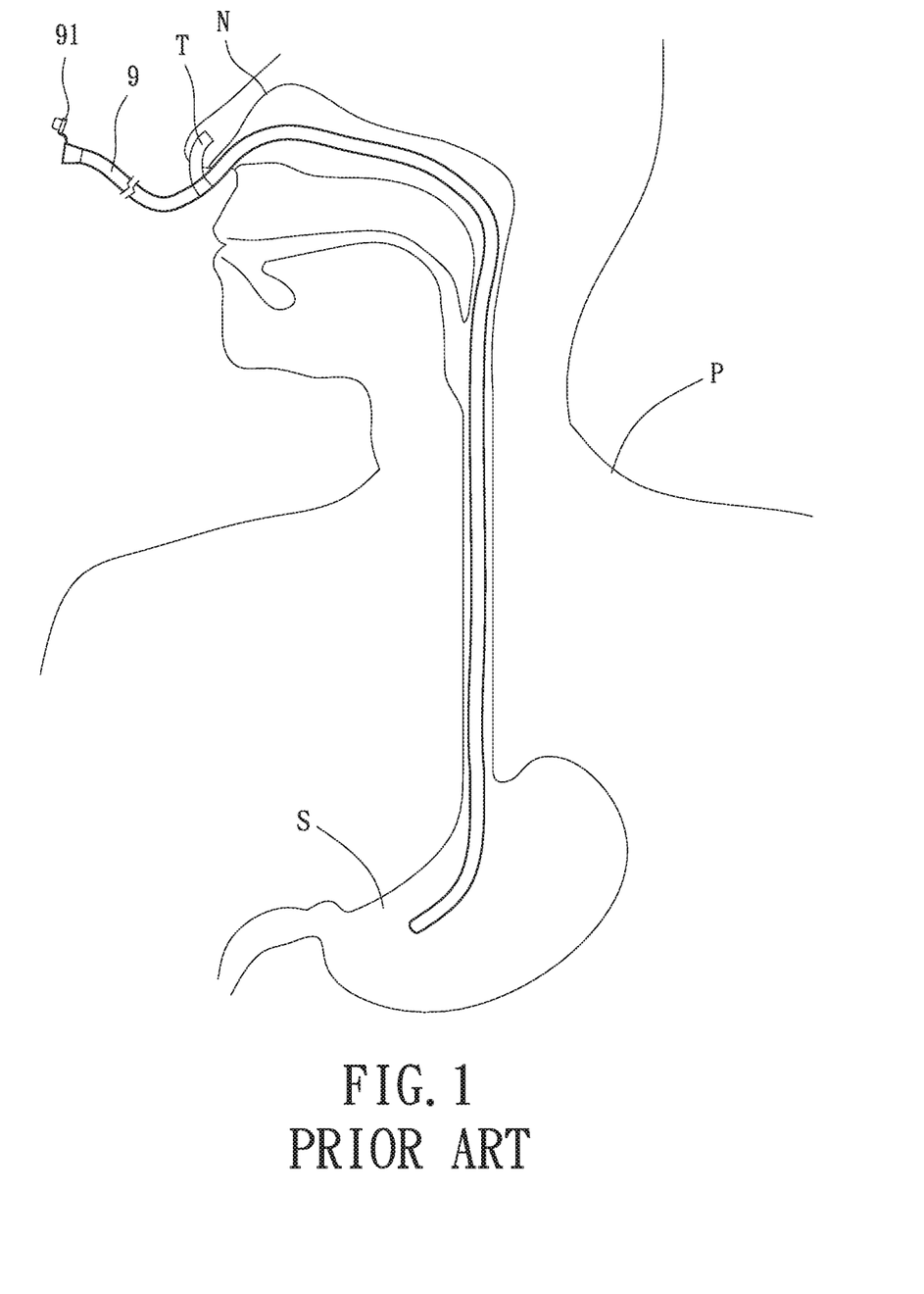
FIG. 1 shows the use of a conventional feeding tube.

FIG. 1 shows a conventional feeding tube 9 which is a hollow tube. The first end of the feeding tube 9 is inserted into the stomach S of the patient P via the nasal cavity N, and the second end of the feeding tube 9 remains outside the nasal cavity N. The second end of the feeding tube 9 is provided with a cap 91. The cap 91 can close the opening of the feeding tube 9 when it is not required to feed the liquid food into the stomach S of the patient P.

Since the second end of the feeding tube 9 (where the cap 91 is) tends to slide into the nasal cavity N, the practitioner needs to keep the second end of the feeding tube 9 outside of the nasal cavity N and to fix the exposed tube to the skin using an adhesive tape T. However, the exposed tube resembles an elephant nose. The presence of the elephant nose and the adhesive tape T causes an unsightly look on the face of the patient, destroying the confidence of the patient and making the patient feel embarrassed in contact with people. Furthermore, the exposed tube can be accidentally pulled during physical activities, causing displacement of the feeding tube 9 and raising safety concerns. This results in confinement of the patient and lowers the willingness of the patient to participate in outdoor activities.

In light of this, it is necessary to improve the conventional feeding tube.

SUMMARY OF THE INVENTION

It is therefore the objective of this invention to provide a concealable feeding tube assembly which, when the feeding is no longer required, permits the exposed tube including the feeding portion to be concealed in the nasal cavity of the patient to avoid causing an unsightly look on the face of the patient and displacement of the feeding tube assembly. In this regard, once the feeding is required, the tube including the feeding portion can be pulled out of the nasal cavity for feeding purposes.

In an aspect, a concealable feeding tube assembly includes a tube and a removable member. The tube has an insertion portion and a feeding portion respectively at two ends thereof The feeding portion is configured for insertion into a nasal cavity of a patient and intercommunicates with the insertion portion. The removable member is detachably attached to the tube and is configured to seal the feeding portion. The removable member includes an abutment portion extending beyond a lateral face of the removable member.

Based on the above, the feeding tube assembly according to the invention allows for concealment of the tube and the feeding portion in the body of the patient and prevents the tube from over-sliding into the nasal cavity through the use of the abutment portion abutting the nose. In addition, the removable member can be turned relatively to the feeding portion to adjust the abutment portion in a position below the nose, thereby concealing the feeding portion below the nose. In this arrangement, when the feeding is not required, the tube and the feeding portion can be completely concealed in the body of the patient without the tube remaining outside the nasal opening and without the use of an adhesive tape. This not only prevents undesired displacement of the tube resulting from the accidental pulling, but also avoids causing an unsightly look on the face of the patient and maintains the confidence of the patient. In this regard, when the feeding is required, the tube can be smoothly pulled out of the nasal cavity through the abutment portion for feeding purposes.

In a form shown, the feeding portion has a dimension of smaller than or equal to 7 mm. In this arrangement, the feeding portion can be concealed in the nasal cavity without exposing it to view and causing the patient to feel uncomfortable, thereby improving comfort in use.

In the form shown, the tube includes an indication portion between the insertion portion and the feeding portion. In this arrangement, the caretaker will not over-pull the tube, thereby improving safety in use.

In the form shown, the indication portion is in a form of a ring having a unique color all over the concealable feeding tube assembly. In this arrangement, the caretaker can be readily aware of the length the tube has been pulled out, thereby preventing the caretaker from over-pulling the tube and improving safety in use.

In the form shown, the indication portion is in a form of a protruding ring. In this arrangement, the caretaker can be readily aware of the length the tube has been pulled out, thereby preventing the caretaker from over-pulling the tube and improving safety in use.

In the form shown, the removable member includes a plug plugged into the feeding portion and abutting an inner periphery of the feeding portion of the tube. The removable member further includes a boundary portion having a same diameter as a maximum diameter of the feeding portion. In this arrangement, the removable member can tightly seal the feeding portion and attaining the easiness of pulling the removable member.

In the form shown, the abutment portion has an end extending beyond the lateral face of the removable member and provided with a hook. In this arrangement, the feeding portion will not over-slide into the nasal cavity of the nose and can be taken out conveniently.

In the form shown, the abutment portion is in a form of a stick having a first end and a second end extending beyond the lateral face of the removable member. Each of the first and second ends of the abutment portion is provided with a hook. In this arrangement, the feeding portion will not over-slide into the nasal cavity of the nose and can be taken out conveniently.

In the form shown, the abutment portion has a first end connected to the lateral face of the removable member, and a second end radially extending outward. In this arrangement, the feeding portion will not over-slide into the nasal cavity of the nose and can be taken out conveniently.

In the form shown, the removable member is coupled with the feeding portion and turns relatively to the feeding portion of the removable member. In this arrangement, the patient can adjust the abutment portion in a position relative to the nose where he/she feels the most comfortable or the removable member is better concealed, improving convenience in use.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

In the various figures of the drawings, the same numerals designate the same or similar parts. Furthermore, when the terms "first", "second", "third", "fourth", "inner", "outer", "top", "bottom", "front", "rear", "axial", "radial", "longitudinal", "transverse", "length", "width", "height" and similar terms are used hereinafter, it should be understood that these terms have reference only to the structure shown in the drawings as it would appear to a person viewing the drawings, and are utilized only to facilitate describing the invention.

DETAILED DESCRIPTION OF THE INVENTION

Figure 2:
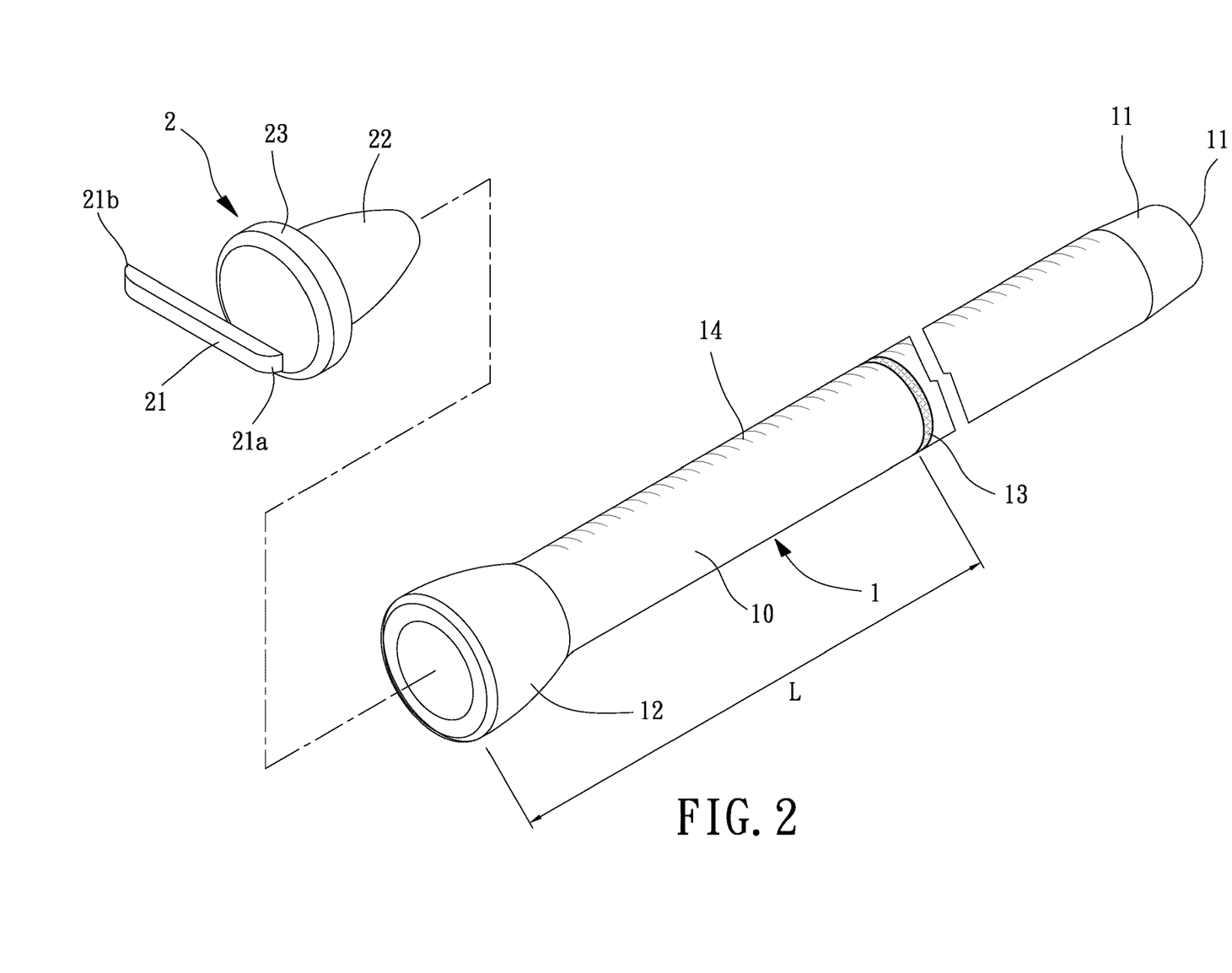
FIG. 2 is an exploded, perspective view of a concealable feeding tube assembly according to a first embodiment of the invention.

FIG. 2 shows a feeding tube assembly according to a first embodiment of the invention. The feeding tube assembly includes a tube 1 and a removable member 2 detachably attached to the tube 1.

The tube 1 has a predetermined length. The tube 1 has a main body 10. The first end of the main body 10 of the tube 1 is provided with an insertion portion 11. The main body 10 of the tube 1 is preferably flexible such that the first end of the feeding tube assembly (where the insertion portion 11 is) can be inserted into the nasal cavity and can remain in the stomach. The insertion portion 11 preferably has a rounded surface 111 which permits the insertion portion 11 to smoothly propel in the gastrointestinal tract of the patient, avoiding hurting the gastrointestinal tract of the patient. The second end of the main body 10 of the tube 1 is provided with a feeding portion 12 intercommunicating with the tube 1. Through the intercommunication therebetween, the liquid food can be injected into the tube 1 through the feeding portion 12, and flows through the tube 1 and the insertion portion 11 and finally into the stomach of the patient. The feeding portion 12 has cross sections perpendicular to a longitudinal axis of the main body 10 of the tube 1 which are preferably circular and have increased diameters, facilitating the injection of the liquid food. The dimension of the feeding portion 12 is preferably smaller than or equal to 7 mm which is slightly smaller than the diameters of the nasal openings. Due to this, the feeding portion 12 will not make the patient feel uncomfortable when concealed in the nasal cavity of the patient.

The main body 10 of the tube 1 preferably includes an indication portion 13 between the insertion portion 11 and the feeding portion 12, forming an indicating distance L between the feeding portion 12 and the indication portion 13. The indicating distance L shows the caretaker the proper distance the tube 1 should be pulled, preventing the caretaker from over-pulling the tube 1 and avoiding withdrawal of the tube 1 from the stomach. The indication portion 13 may have a noticeable color or may be in the form of a protruding ring which can be readily recognized by the caretaker. Alternatively, the indication portion 13 has a different color from the main body 10; namely, the indication portion 13 has a unique color over the main body 10. The invention is not limited to either option. In this arrangement, the caretaker can be readily aware of the length the tube 1 has been pulled out, effectively preventing the caretaker from over-pulling the tube 1. In addition, the main body 10 of the tube 1 can be provided with graduations 14 that allow the caretaker to observe and record the depth of the tube 1.

The removable member 2 can be attached to or detached from the feeding portion 12 of the tube 1. The removable member 2 can close the feeding portion 12 to prevent the backflow of the liquid from the stomach or the tube 1. The removable member 2 includes an abutment portion 21 extending beyond a lateral face of the removable member 2, permitting the removable member 2 to abut the nose (i.e. underneath the nasal septum). Therefore, the feeding portion 12 of the tube 1 can remain below the nasal opening, avoiding difficulty in taking the feeding portion 12 out of the nasal cavity resulting from excessive slide of the feeding portion 12 into the nasal cavity. In this embodiment, the abutment portion 21 is in the form of a short stick. The first end 21a of the abutment portion 21 may be integrally formed with the removable member 2 such that the second end 21b of the abutment portion 21 is laterally outward of the removable member 2.

Specifically, the removable member 2 includes a plug 22 plugged into the feeding portion 12 and abutting the inner periphery of the feeding portion 12, thereby closing the feeding portion 12. The removable member 2 further includes a boundary portion 23 which preferably has the same diameter as the maximum diameter of the feeding portion 12. The boundary portion 23 can be concealed in the nasal cavity without exposing it to view and without causing the patient to feel uncomfortable. In another embodiment, the removable member 2 is coupled with the feeding portion 12 by ways of fastening and/or screwing commonly adopted in prior art. The invention is not limited to any of these options.

Figure 3:
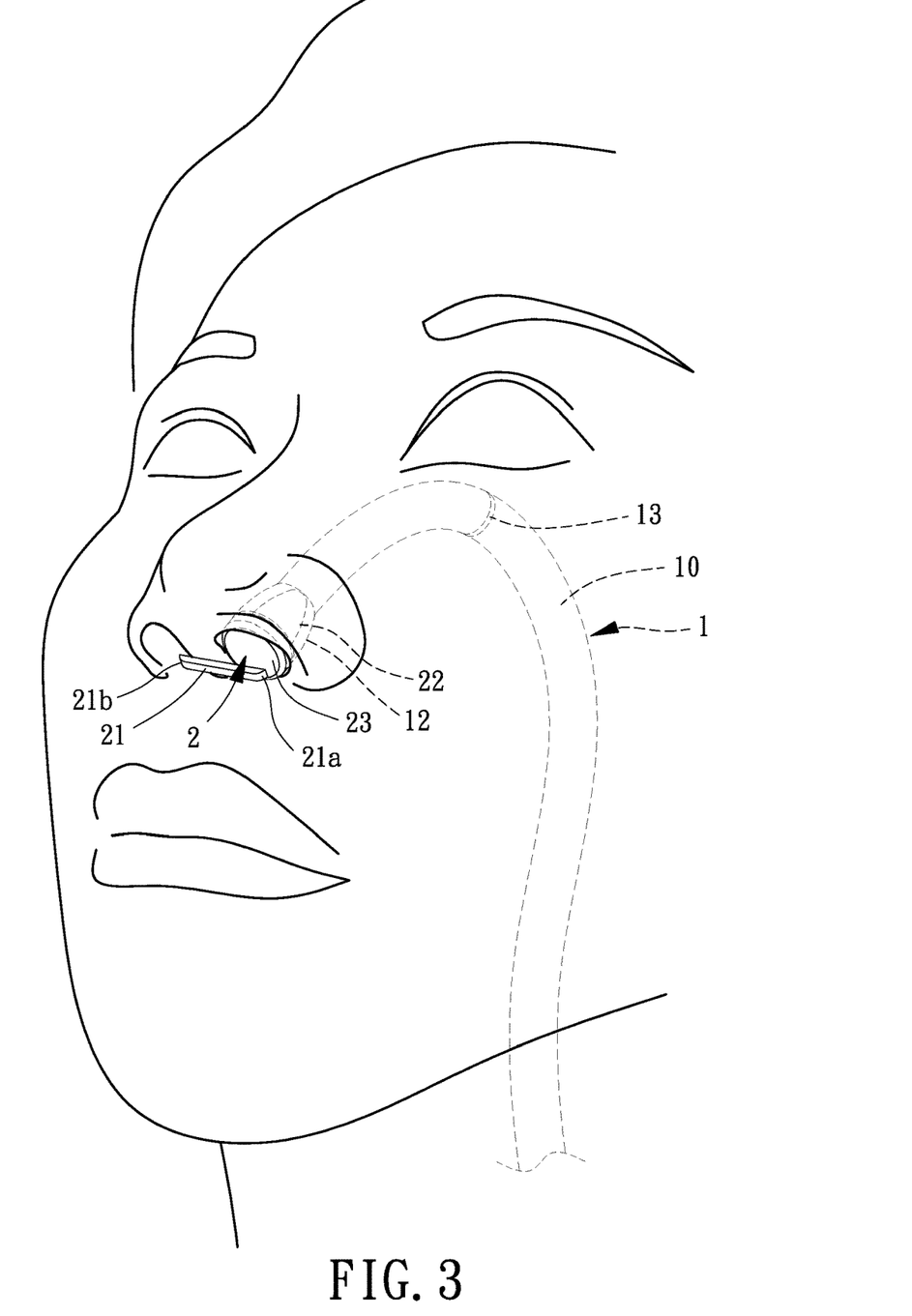
FIG. 3 shows the concealable feeding tube assembly in a retracted state where feeding is not required according to the first embodiment of the invention.

Referring to FIGS. 2 and 3, based on the above structures, the proper length of the tube 1 is determined according to the distance between the nasal opening and the xiphoid process in the thorax cavity. Then, the practitioner attaches the removable member 2 to the feeding portion 12 of the tube 1 and inserts the insertion portion 11 of the tube 1 into the stomach of the patient through the nasal cavity and the esophagus. Next, the practitioner pushes the tube 1 further into the stomach until the feeding portion 12 is retracted into the nasal cavity and concealed near the nasal opening. According to the above, the tube 1 and the feeding portion 12 can be concealed in a space between the nasal openings and the stomach. In this regard, the practitioner pivots the abutment portion 21 about a central axis of the feeding portion 12 to position the abutment portion 21 in a proper position abutting the nose underneath the nasal septum, thereby hiding the abutment portion 21 below the nose and fixing the feeding portion 12 of the tube 1 in place. Thus, the feeding portion 12 of the tube 1 will not slide into the nasal cavity too deep. After the insertion of the feeding tube assembly according to the present invention, the tube 1 can be concealed in the body of the patient without remaining outside the nasal cavity and without using an adhesive tape, advantageously maintaining the look of the face of the patient and their self-respect as well as preventing the patient from accidentally pulling the tube 1 during the physical activities. Besides, the patient can turn the removable member 2 by himself/herself to adjust the removable member 2 in a position where he/she feels the most comfortable or the removable member 2 is better concealed.

Figure 4:
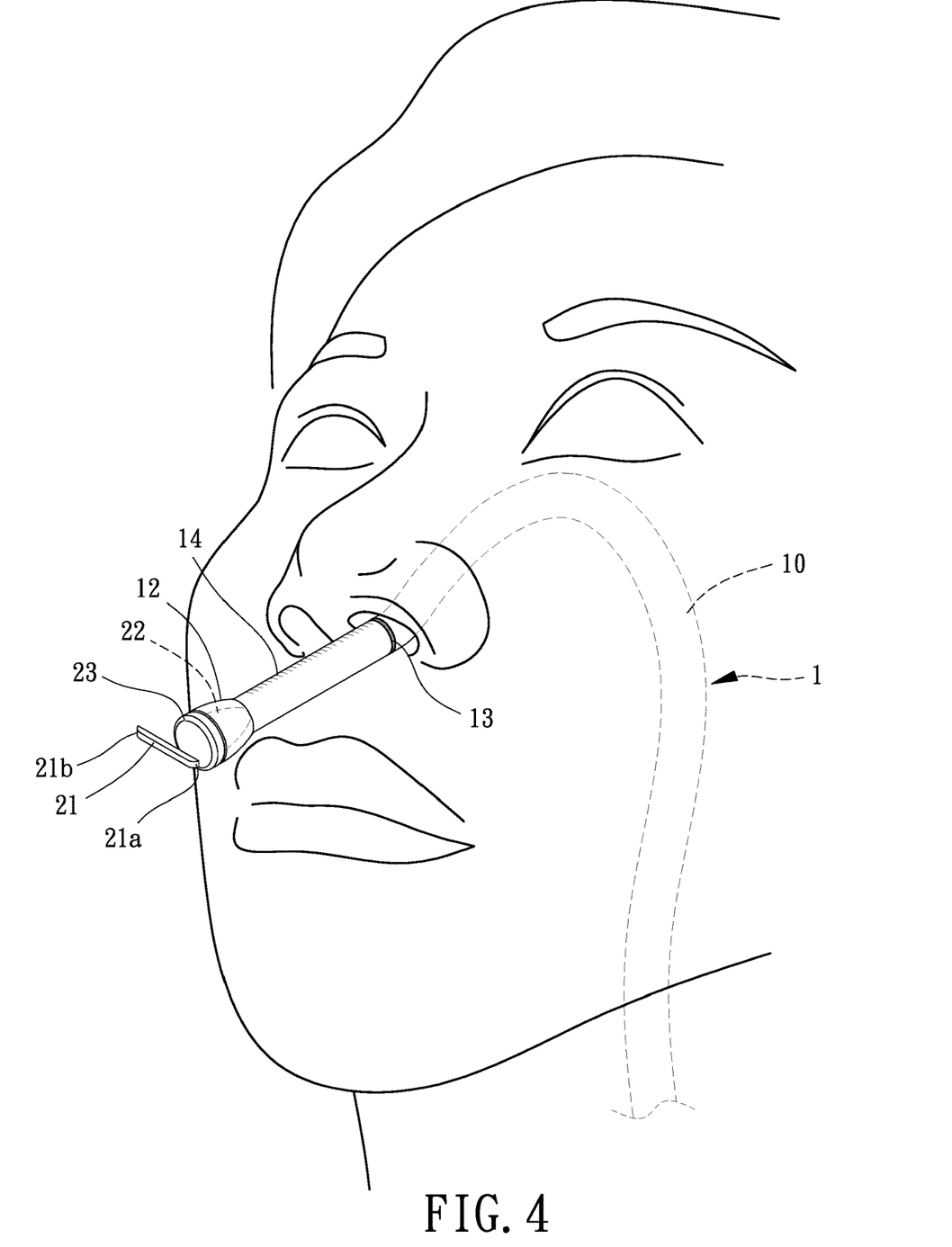
FIG. 4 shows the concealable feeding tube assembly in use for the feeding purpose according to the first embodiment of the invention.

Referring to FIGS. 2 and 4, when the feeding is required, the caretaker can pull the feeding portion 12 out of the nasal cavity with the indication portion 13 remaining in the nasal cavity. This prevents the insertion portion 11 from being pulled out of the stomach. After the tube 1 is pulled in a proper distance, the caretaker can detach the removable member 2 from the feeding portion 12 and inject the liquid food into the feeding portion 12 using a syringe. The liquid food can flow into the stomach to supply the required nutrition to the patient.

Referring to FIG. 3, following the injection of the liquid food and a clean of the feeding tube assembly, the caretaker can attach the removable member 2 back to the tube 1 to prevent the liquid food or stomach juice from flowing back to the feeding portion 12. Next, the feeding portion 12 is pushed back into the nasal cavity until the second end 21*b* of the removable member 2 abuts the nose, thus concealing the tube 1 and the feeding portion 12 between the nasal openings and the stomach. Since the abutment portion 21 abuts the nose underneath the nasal septum, the abutment portion 21 can be concealed from viewing.

Figure 5:
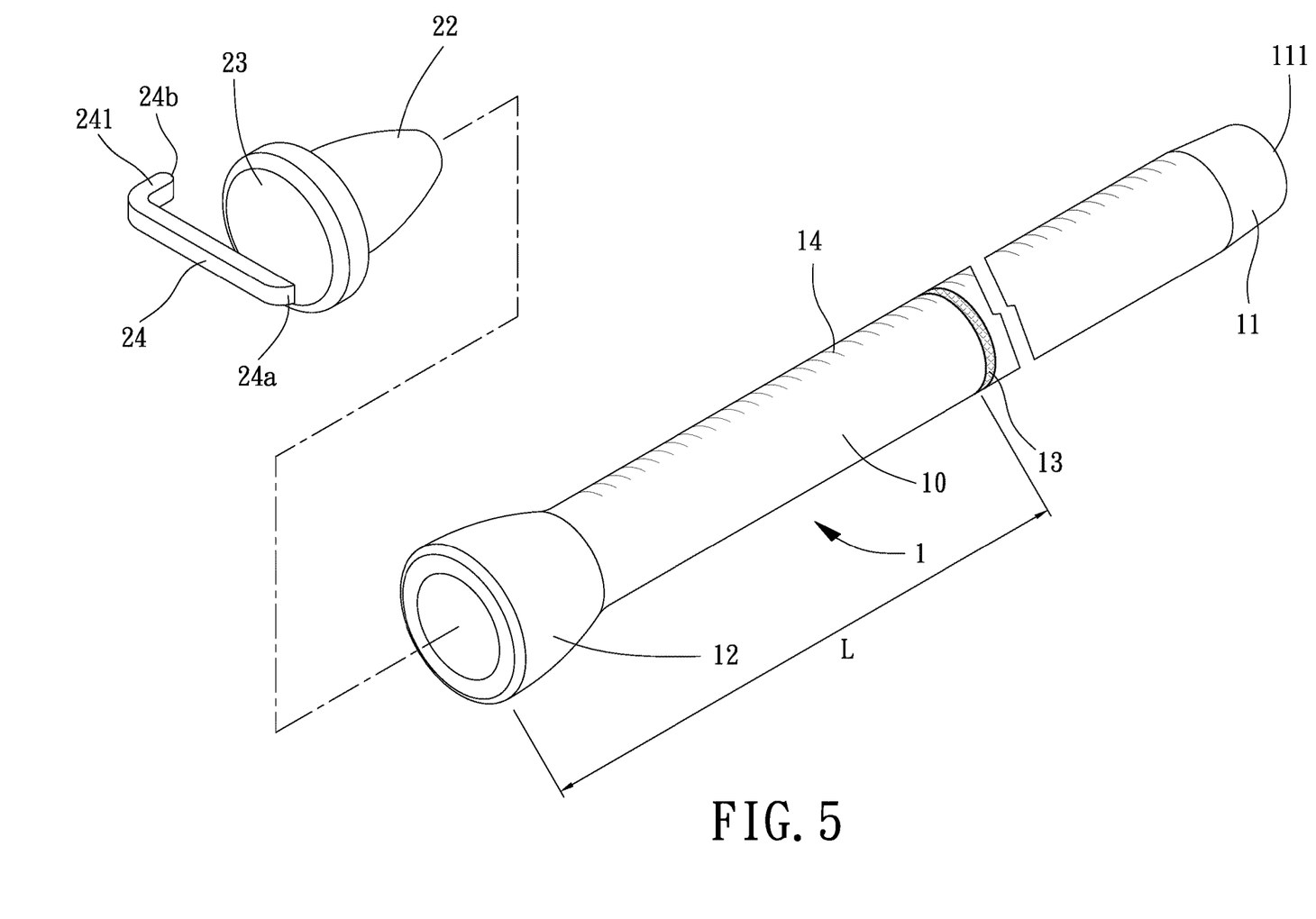
FIG. 5 is an exploded, perspective view of a concealable feeding tube assembly according to a second embodiment of the invention.
Figure 6:
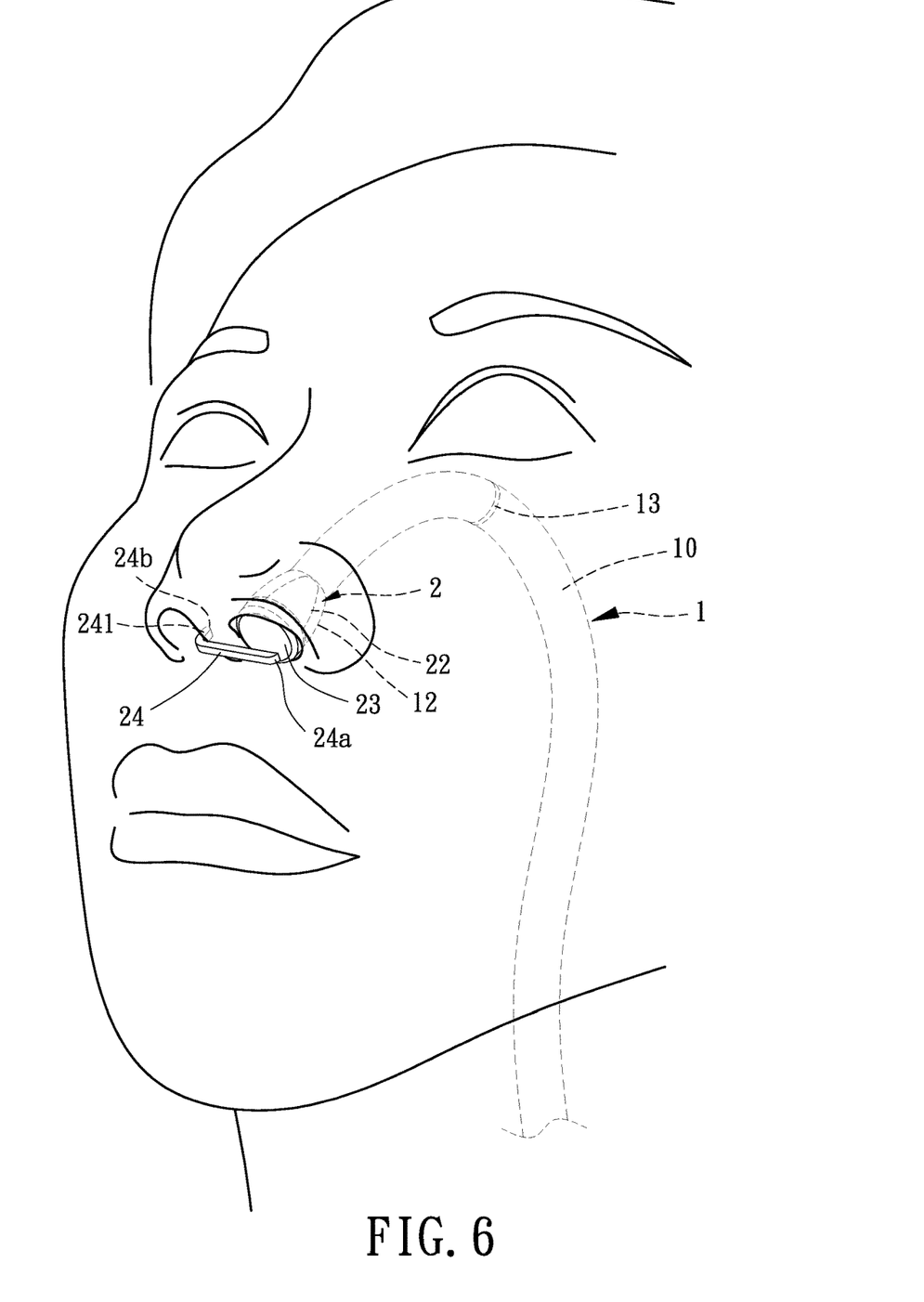
FIG. 6 shows the concealable feeding tube assembly in a retracted state where feeding is not required according to the second embodiment of the invention.

FIGS. 5 and 6 show a feeding tube assembly according to a second embodiment of the invention. In this embodiment, the second end 24*b* of the abutment portion 24 is provided with a hook 241. The hook 241 is fastened with the wings of the nose or extends into the other nasal opening where the removable member 2 is absent, preventing the feeding portion 12 from over-sliding into the nasal cavity. As a result, the feeding portion 12 can be smoothly pulled out of the nasal cavity.

Figure 7:
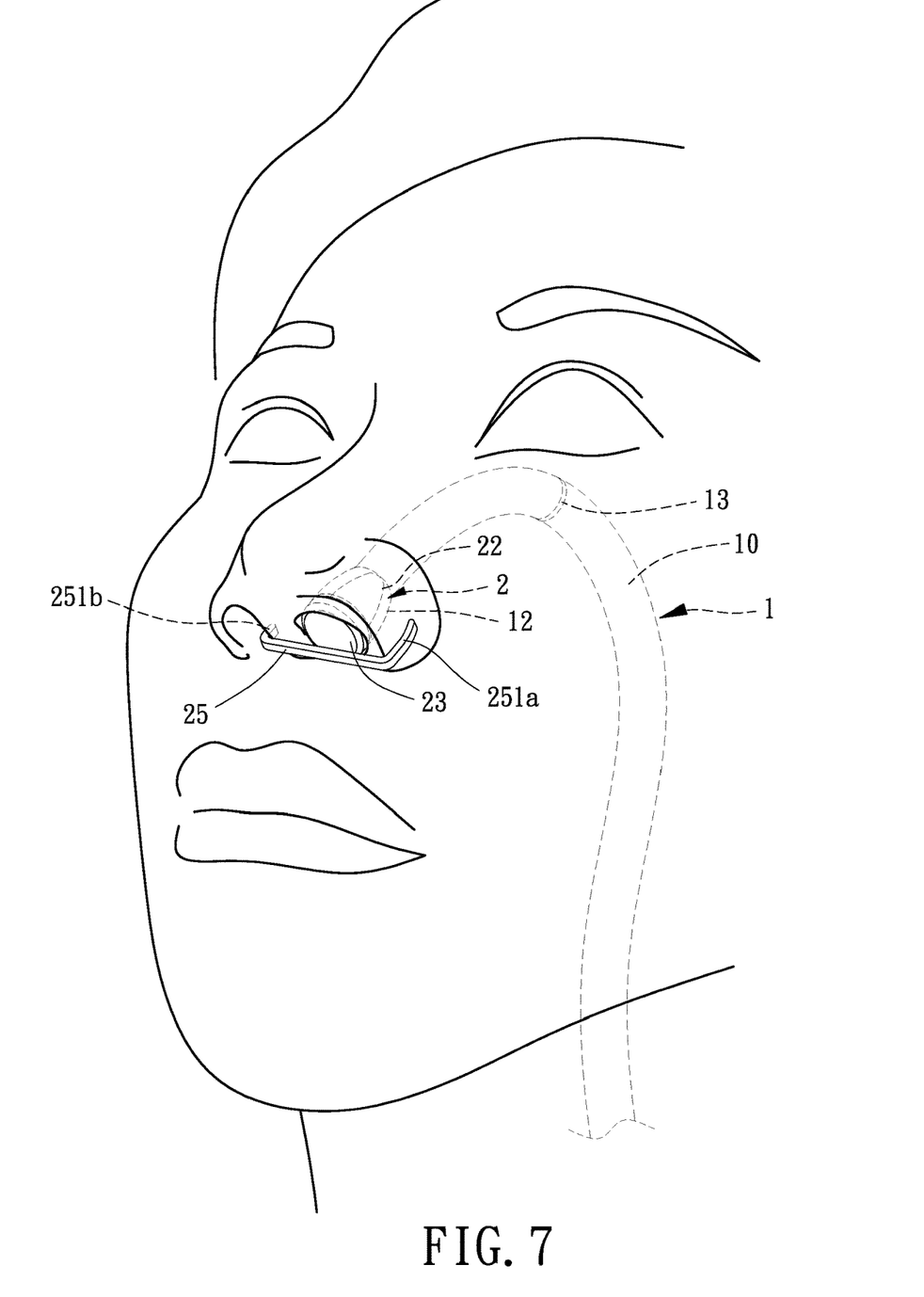
FIG. 7 shows a concealable feeding tube assembly in a retracted state where feeding is not required according to a third embodiment of the invention.

FIG. 7 shows a feeding tube assembly according to a third embodiment of the invention. In this embodiment, the abutment portion 25 includes two hooks 251*a*, 251*b*. Both the first and second ends of the abutment portion 25 extend beyond the lateral face of the removable member 2 and are provided with a respective hook 251*a*, 251*b*. One of the hooks 251*a*, 251*b* is fastened with the other nasal opening and the other is fastened with the wing of the nose. Alternatively, the two hooks 251*a*, 251*b* are respectively fastened with the wings of the nose. The arrangement of the hooks 251*a*, 251*b* can reinforce the ability of the removable member 2 to prevent the tube 1 from over-sliding into the nasal cavity and thereby ensuring an easiness of pulling-out the removable member 2. This avoids a non-uniform pressure distribution over the nose where the abutment portion 25 applies pressure to only one side of the nose, improving comfort in use over a long duration of time.

Figure 8:
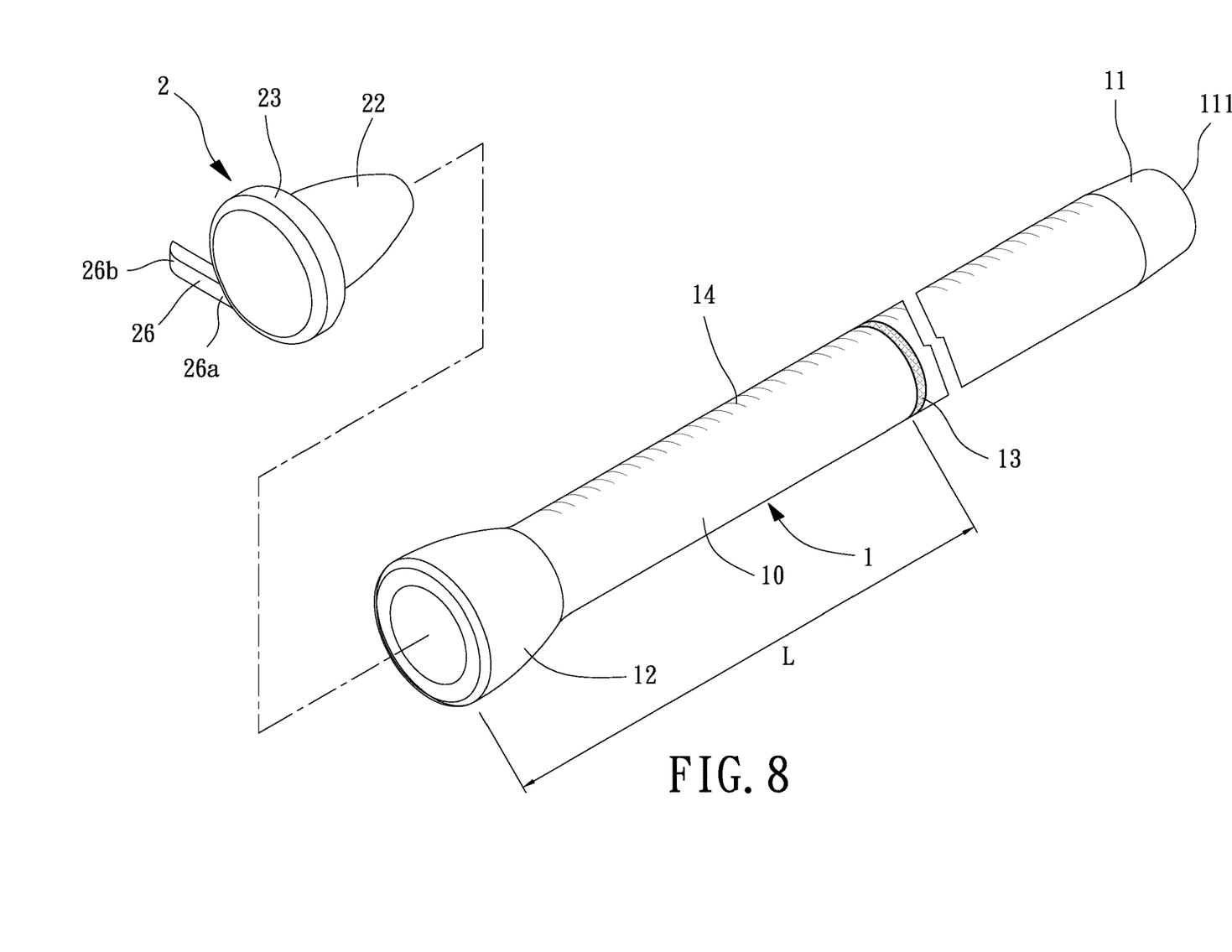
FIG. 8 is an exploded, perspective view of a concealable feeding tube assembly according to a fourth embodiment of the invention.
Figure 9:
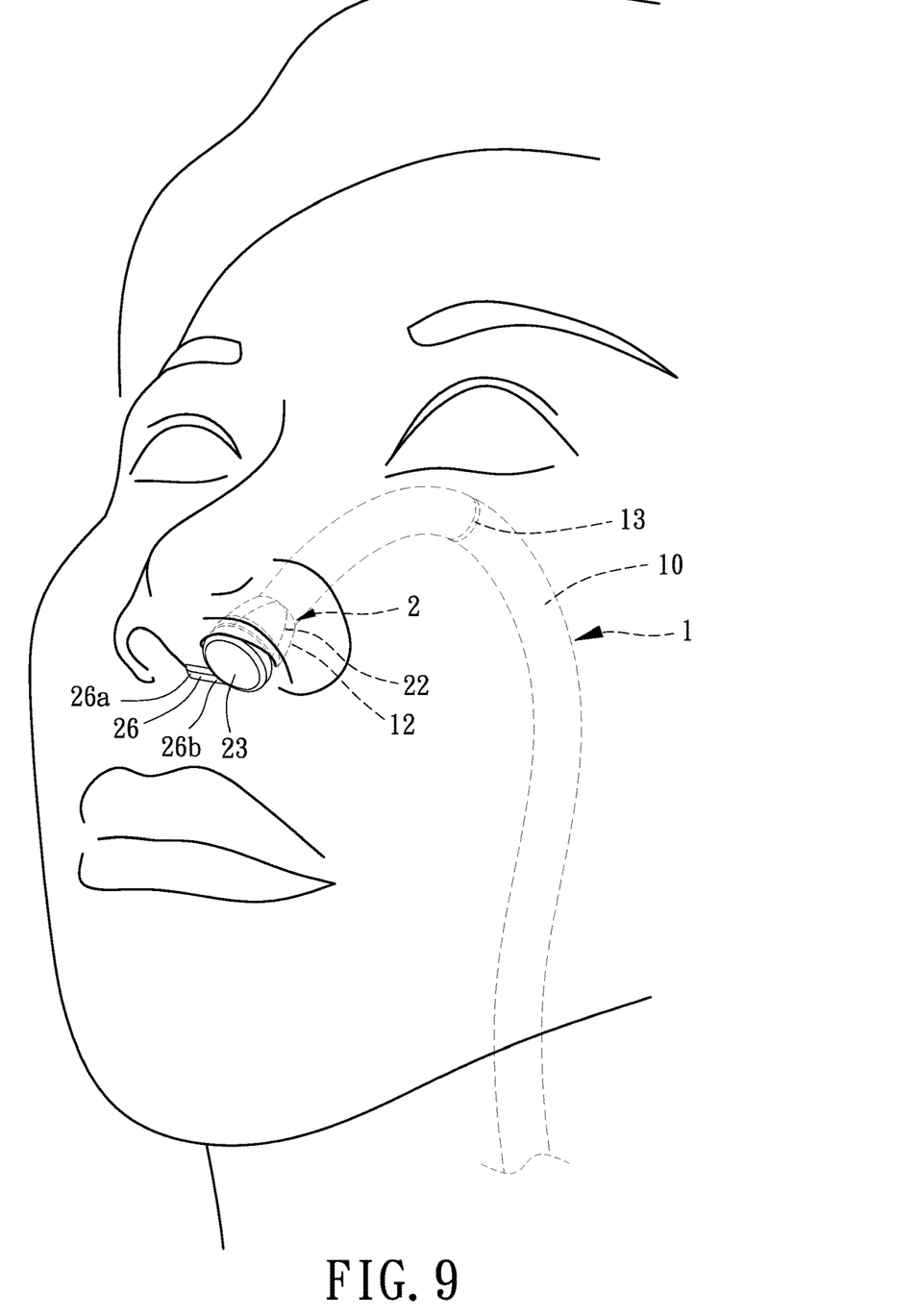
FIG. 9 shows the concealable feeding tube assembly in a retracted state where feeding is not required according to the fourth embodiment of the invention.
Figure 10A:
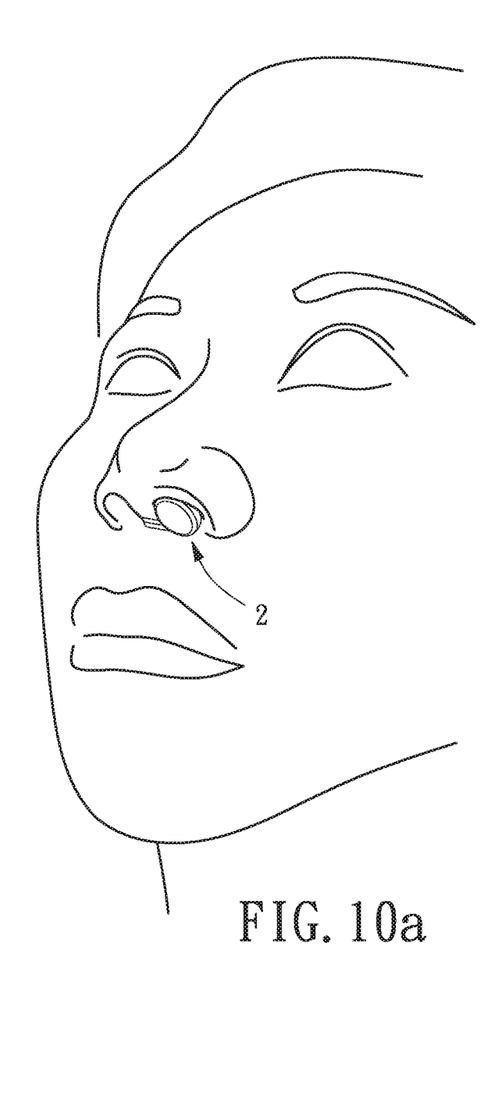
FIGS. 10a and 10b show a comparison in use between the proposed feeding tube assembly of the fourth embodiment of the invention and the conventional feeding tube.
Figure 10B:
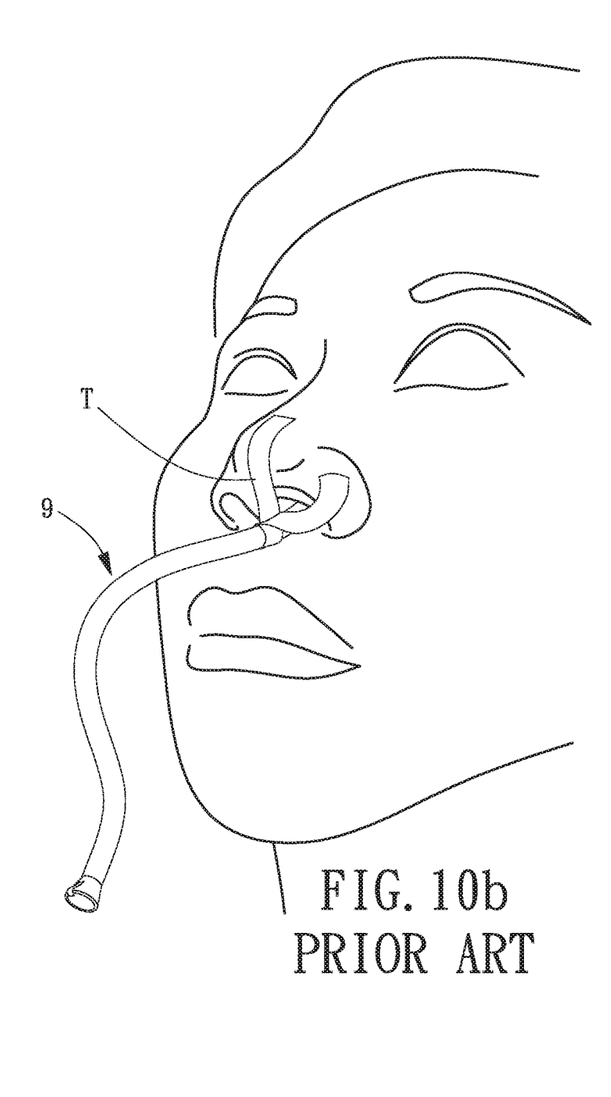

FIG. 8 shows a feeding tube assembly according to a fourth embodiment of the invention. In this embodiment, the first end 26*a* of the abutment portion 26 is integrally formed with a lateral face of the boundary portion 23 of the removable member 2, such that the second end 26*b* of the abutment portion 26 radially extends outward. Referring to FIG. 9, the second end 26*b* of the abutment portion 26 can abut the nose underneath the nasal septum, ensuring that the feeding portion 12 will not over-slide into the nasal cavity and thereby achieving an easiness of pulling-out the feeding portion 12. Besides, the abutment portion 26 is relatively shorter compared with those in the previous embodiments, improving the concealment of the abutment portion 26. FIGS. 10*a* and 10*b* show a comparison in use between the proposed feeding tube assembly of the fourth embodiment of the invention and the conventional feeding tube.

In summary, the feeding tube assembly according to the invention allows for concealment of the tube and the feeding portion in the body of the patient and prevents the tube from over-sliding into the nasal cavity through the use of the abutment portion abutting the nose. In addition, the removable member can be turned relative to the feeding portion to adjust the abutment portion in a position below the nose, thereby concealing the feeding portion below the nose. In this arrangement, when the feeding is not required, the tube and the feeding portion can be completely concealed in the body of the patient without the tube remaining outside the nasal opening and without the use of an adhesive tape. This not only prevents undesired displacement of the tube resulting from the accidental pulling, but also avoids causing an unsightly look on the face of the patient and maintains the confidence of the patient. In this regard, when the feeding is required, the tube can be smoothly pulled out of the nasal cavity through the abutment portion for feeding purposes. In addition, the arrangement of the indication portion helps the caretaker readily recognize the length the tube has been pulled out, advantageously preventing the caretaker from over-pulling the tube.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. A concealable feeding tube assembly comprising:
   a tube having a main body with an insertion portion and a feeding portion respectively at two ends thereof, wherein the feeding portion is configured for insertion into a first nasal cavity of a patient, wherein the main body intercommunicates with the insertion portion and the feeding portion; and a removable member detachably attached to the tube and configured to seal the feeding portion, wherein the removable member comprises an abutment portion extending beyond a lateral face of the removable member;

wherein:

the removable member comprises a plug and a boundary portion, the plug and the boundary portion are physically connected to each other, and the abutment portion is physically connected to the boundary portion;

when the removable member seals the feeding portion, the plug is plugged into the feeding portion and abuts an inner periphery of the feeding portion, and the abutment portion is configured to abut a position underneath a nasal septum;

the abutment portion has a first surface and a second surface opposite to the first surface, the first surface is more adjacent to the plug than the second surface, and the abutment portion has a first end bent toward the first surface to form a hook; and when the plug is plugged into the feeding portion and abuts the inner periphery of the feeding portion, the hook is configured to be fastened outside wings of a nose or on an inner wall of a second nasal cavity of the patient where the removable member is absent.

2. The concealable feeding tube assembly as claimed in claim 1, wherein the feeding portion has a dimension of smaller than or equal to 7 mm.

3. The concealable feeding tube assembly as claimed in claim 1, wherein the tube includes an indication portion between the insertion portion and the feeding portion.

4. The concealable feeding tube assembly as claimed in claim 3, wherein the indication portion is in a form of a ring encircling the main body and having a different color from the main body.

5. The concealable feeding tube assembly as claimed in claim 3, wherein the indication portion is in a form of a protruding ring.

6. The concealable feeding tube assembly as claimed in claim 1, wherein the boundary portion has a same diameter as a maximum diameter of the feeding portion.

7. The concealable feeding tube assembly as claimed in claim 1, wherein the abutment portion is in a form of a stick having the first end and a second end extending beyond the lateral face of the removable member, and wherein the second end of the abutment portion is provided with a hook.

8. The concealable feeding tube assembly as claimed in claim 1, wherein the abutment portion has a second end connected to a lateral face of the boundary portion of the removable member, and the first end extending outward in an extending direction perpendicular to an axial direction of the feeding portion of the tube.

9. The concealable feeding tube assembly as claimed in claim 1, wherein when the removable member is coupled with the feeding portion, the removable member is configured to turn relative to the feeding portion.

* * * * *